(12) United States Patent
Brodkin et al.

(10) Patent No.: US 12,097,328 B2
(45) Date of Patent: Sep. 24, 2024

(54) APPARATUS AND METHOD FOR MONITORING THE DEGREE OF INTEGRATION BETWEEN THE FUNCTIONS OF THE HEART AND THE LUNGS, AND THE THERAPEUTIC SUCCESS OF RESUSCITATIVE INTERVENTIONS

(71) Applicants: Ian Brodkin, Vancouver (CA); Arthur Willms, Surrey (CA); Fouad Halwani, Kirkland (CA); Awni Ayoubi, Surrey (CA); Nathan Ayoubi, Vancouver (CA)

(72) Inventors: Ian Brodkin, Vancouver (CA); Arthur Willms, Surrey (CA); Fouad Halwani, Kirkland (CA); Awni Ayoubi, Surrey (CA); Nathan Ayoubi, Vancouver (CA)

(*) Notice: Subject to any disclaimer, the term of this patent is extended or adjusted under 35 U.S.C. 154(b) by 322 days.

(21) Appl. No.: 16/592,642

(22) Filed: Oct. 3, 2019

(65) Prior Publication Data
US 2020/0101254 A1    Apr. 2, 2020

Related U.S. Application Data

(63) Continuation of application No. 15/914,922, filed on Mar. 7, 2018, now abandoned, which is a
(Continued)

(51) Int. Cl.
*A61M 16/08*    (2006.01)
*A61B 5/08*    (2006.01)
(Continued)

(52) U.S. Cl.
CPC ....... *A61M 16/0816* (2013.01); *A61B 5/0816* (2013.01); *A61B 5/087* (2013.01);
(Continued)

(58) Field of Classification Search
None
See application file for complete search history.

(56) References Cited

U.S. PATENT DOCUMENTS

| 4,413,632 A | * | 11/1983 | Schlessinger | .......... | A61B 5/083 |
| | | | | | 600/529 |
| 4,989,456 A | * | 2/1991 | Stupecky | ............. | A61B 5/0876 |
| | | | | | 138/46 |

(Continued)

OTHER PUBLICATIONS

International Preliminary Report on Patentability from PCT Application No. PCT/CA2010/000684, dated Jul. 11, 2011, 3 pages.
(Continued)

*Primary Examiner* — Michael R Bloch
(74) *Attorney, Agent, or Firm* — Klarquist Sparkman, LLP

(57) ABSTRACT

A method, system and apparatus for assessing the coupling between lung perfusion and ventilation in a patient who is mechanically ventilated or who is breathing spontaneously through a conventional artificial airway is provided. Embodiments of the apparatus comprise an adaptor configured to fit between the artificial airway and mechanical ventilator, a measuring chamber in constant fluid communication with the adaptor via one or more measuring chamber sampling ports, and a monitoring unit where data obtained from temperature and relative humidity sensors located in the measuring is calibrated, sampled, logged and analyzed together with anthropometric patient data to display a coupling index Qi and to enable ongoing diagnostic cardio-pulmonary monitoring of a patient by comparing changes in the patient's index during a monitoring interval.

7 Claims, 2 Drawing Sheets

Related U.S. Application Data continuation of application No. 13/266,747, filed as application No. PCT/CA2010/000684 on Apr. 27, 2010, now abandoned.

(60) Provisional application No. 61/173,136, filed on Apr. 27, 2009.

(51) Int. Cl.
| | | |
|---|---|---|
| *A61B 5/087* | (2006.01) | |
| *A61B 5/097* | (2006.01) | |
| *A61M 16/00* | (2006.01) | |
| *A61M 16/16* | (2006.01) | |
| *A61B 5/00* | (2006.01) | |
| *A61B 5/01* | (2006.01) | |

(52) U.S. Cl.
CPC ............ *A61B 5/0878* (2013.01); *A61B 5/097* (2013.01); *A61M 16/0051* (2013.01); *A61M 16/021* (2017.08); *A61M 16/161* (2014.02); *A61B 5/01* (2013.01); *A61B 5/7285* (2013.01); *A61M 2016/0036* (2013.01); *A61M 16/0858* (2014.02); *A61M 2205/3368* (2013.01); *A61M 2205/505* (2013.01); *A61M 2205/70* (2013.01)

(56) References Cited

U.S. PATENT DOCUMENTS

| | | | | |
|---|---|---|---|---|
| 5,005,582 | A | | 4/1991 | Serikov et al. |
| 5,178,155 | A | * | 1/1993 | Mault .................... A61B 5/083 600/531 |
| 6,039,696 | A | | 3/2000 | Bell |
| 6,954,702 | B2 | * | 10/2005 | Pierry .................... A61B 5/083 422/94 |
| 8,190,249 | B1 | * | 5/2012 | Gharieb ................. A61B 5/318 600/544 |
| 2004/0073098 | A1 | * | 4/2004 | Geva ........................ A61B 5/24 600/300 |
| 2007/0107728 | A1 | * | 5/2007 | Ricciardelli ........... A61B 5/091 128/204.21 |
| 2007/0149862 | A1 | * | 6/2007 | Pipke ................... A61B 5/7264 600/301 |
| 2009/0306528 | A1 | * | 12/2009 | Curti .................... A61B 5/0878 600/537 |

OTHER PUBLICATIONS

International Search Report from PCT Application No. PCT/CA2010/000684, dated Aug. 27, 2010, 2 pages.

Serikov et al., "Pulmonary and bronchial circulations: contributions to heat and water exchange in isolated lungs." *Journal of Applied Physiology* 91(5): 1977-1985, 2001.

* cited by examiner

APPARATUS AND METHOD FOR MONITORING THE DEGREE OF INTEGRATION BETWEEN THE FUNCTIONS OF THE HEART AND THE LUNGS, AND THE THERAPEUTIC SUCCESS OF RESUSCITATIVE INTERVENTIONS

CROSS REFERENCE TO RELATED APPLICATIONS

This application is a continuation of U.S. patent application Ser. No. 15/914,922, filed Mar. 7, 2018, which is continuation of U.S. patent application Ser. No. 13/266,747, filed Feb. 1, 2012, now abandoned, which is the U.S. National Stage of International Application No. PCT/CA2010/000684, filed Apr. 27, 2010, which in turn claims priority to and the benefit of U.S. Provisional Application No. 61/173,136, filed Apr. 27, 2009. The prior applications are incorporated herein by reference in their entirety.

FIELD

The presently disclosed subject matter relates to methods, systems and apparatus for measuring the temperature and humidity of inhaled and exhaled gases in the respiratory tract.

BACKGROUND

Taken in isolation, the clinical assessment of physiological variables used to monitor patient condition (e.g. requirements for supplemental oxygen, composition of exhaled gases, blood pressure, heart rate, etc.) is often open to misinterpretation. These variables are frequently interdependent, and misinterpretation of their individual variations may result in delay in the timely detection of a change in status and subsequent diagnosis, and in the appropriate treatment of a patient. Wrong clinical management decisions may also be made when changes in vital signs are misleading due to diseases or injuries having similar clinical manifestations.

Several devices have been developed to measure temperature and humidity in the tracheo-bronchial tree and in the upper airways in humans, and some of these have attempted to derive specific quantitative values such as, for example, cardiac output. However, prior efforts in this area have primarily addressed specific problems related to the way that ambient temperature and humidity affect long-term ventilation via tracheostomy, and have generally produced devices and methods suitable for laboratory research purposes only. Consequently, such devices have never become a part of routine patient care.

SUMMARY

The function of the heart and the lungs are interdependent and are affected by the changing conditions in the rest of the body. A reliable, easy to use, real-time, non-invasive or minimally invasive system for assessment of cardio-pulmonary status by an analytical and predictive instrument that does not require expert interpretation of physiological parameters would accordingly be of high clinical value. Making this kind of artificial intelligence available to those who care for hospitalized and ambulatory patients would represent a significant advancement in the improvement of clinical outcomes.

The presently disclosed and claimed subject matter accordingly provides a method, system and apparatus for assessing the coupling between lung perfusion and ventilation in a patient who is mechanically ventilated or who is breathing spontaneously through a conventional artificial airway (such as an endrotracheal tube or tracheostomy tube). Embodiments of the present apparatus comprise an adaptor configured to fit between the artificial airway and mechanical ventilator (or simply to attach to the free end of the artificial airway in cases where the patient is breathing spontaneously), a measuring chamber in constant fluid communication with the adaptor via one or more measuring chamber sampling ports, and a monitoring unit where data obtained from temperature and relative humidity sensors located in the measuring chamber (and in some embodiments together also with data obtained from spirometry and/or reference temperature and reference relative humidity sensors associated with the monitoring unit) is calibrated, sampled, logged and analyzed together with anthropometric patient data provided by the operator in order to, inter alia, calculate and/or derive a novel cardio-pulmonary coupling index termed "Qi" as described herein below, and to enable ongoing diagnostic cardio-pulmonary monitoring of a patient by comparing changes in the patient's Qi index during a monitoring interval. The Qi index is expressed in non-dimensional units, and is displayed relative to a range of "normal" values defined with reference to values that are commonly observed at rest in persons in good general health and who generally match a given patient in gender, age and body size, and/or as a specific patient's baseline values at rest or under stress at the outset of a monitoring interval.

The measuring chamber is preferably located adjacent to (or as close as possible to) the end of the artificial airway in order to minimize heat losses, and is disposed out of the main path of airflow through the adaptor into and from the lungs to reduce the possibility of mucosal secretions or other substances interfering with the functioning of the sensors. In preferred embodiments, the measuring chamber is positioned above the adaptor during use to further reduce the possibility of such interference.

To optimize the response time of the sensors and to further reduce heat losses, measuring chamber architecture may comprise one or more ducted paths through which air that is drawn through the sampling port or ports enters the measuring chamber. Ideally, the ducted paths are pointed directly at the sensors and (to simplify calculations) are sized to maintain the same gas/air flow speed as in the main artificial airway, or a predetermined ratio thereof. Heating resistors located in the ducted paths may also preferably be used to compensate for minor heat losses that may occur during the transfer of air from the adaptor to the measuring chamber, to intercept and evaporate mucous reaching the ducts, to remove condensation that may have occurred inside the measuring chamber before a sensor reading is taken (in order to minimize evaporation-induced measurement errors), to remove condensation from the tubing that links the measuring chamber and the monitoring unit (in order to prevent a build-up of moisture in the tubing that could interfere with pump operation), and/or to displace (i.e. to lower) the relative humidity levels of the air in the measuring chamber by a specific selected amount to improve the performance of the relative humidity sensor.

The adaptor and measuring chamber may be formed as a single unitary assembly, or may be formed from separate moldings or castings, and in preferred embodiments both adaptor and measuring chamber are formed of clear rigid plastic and provided in a clean or sterile single-use package to prevent or reduce the risk of patient cross contamination. The measuring chamber walls preferably include one or more molded-in plano-convex or double-convex lenses positioned to provide an enlarged view of the temperature sensor, the measuring surface of the relative humidity sensor, and the heating resistors. A Light Emitting Diode (LED) may also be positioned within the measuring chamber to illuminate the temperature and relative humidity sensors. These features allow an operator to readily check for the presence of mucous or other undesirable matter on the sensors or resistors. The intensity of the LED may be also modulated to provide some heating to compensate for heat losses across the measuring chamber walls.

In some embodiments, an optional auxiliary adaptor that includes a flexible membrane to create pressure differentials by resisting airflow therethrough, as well as an outlet for draining away airway secretions, is fitted to the airway side of the main adaptor. The pressure differentials generated by the airflow against the flexible membrane are monitored and utilized by a conventional spirometry module located in the monitoring unit to calculate tidal volume and/or minute volume (i.e. the volume of gas moved into and out of the lungs in one minute). In cases where the patient is being mechanically ventilated, these volumes may alternatively be calculated or obtained directly from the mechanical ventilator. In further alternative, these volumes may be obtained or estimated in other ways known to those of skill in the art, and manually inputted into the system by the operator.

The measuring chamber and the optional auxiliary adaptor are connected to the monitoring unit by single use or reusable (e.g. autoclavable) tubing, and by conventional wiring and connectors for connecting the sensors and other components of the measuring chamber and the optional auxiliary adaptor to corresponding componentry of the monitoring unit. The monitoring unit comprises a suction system; processing and control circuitry under the control of software instructions for the calibration, sampling, logging and analysis of data obtained from the temperature and relative humidity sensors, from the optional auxiliary adaptor, and from the operator of the apparatus; display and data entry means such as an LCD touch screen or a more conventional display and keyboard; and associated electromechanical controls including relays and solenoids as described further herein below.

In addition to the derivation of coupling index Qi and the general diagnostic cardio-pulmonary monitoring of a patient by comparison of the patient's Qi index during a monitoring interval as noted above, the processing and control circuitry of the monitoring unit may be controlled by software instructions to:

a—carry out calibration processes in relation to the temperature and relative humidity sensors;

b—sample, log and analyze the temperatures and humidities of inhaled and exhaled gases as measured by the sensors, and calculate and apply suitable correction factors to compensate for residual heat losses between the sampling port(s) and the sensors;

c—detect the breathing cycle by, for example, detecting successive moments at which sampled air temperatures peak and start to decrease (indicating an inhalation start), or by detecting the moment of pressure readings reversal from the optional auxiliary adaptor data (indicating the switch from inhalation to exhalation or the opposite), and synchronize the sampling therewith;

d—sample, log and analyze the pressure differentials in the optional auxiliary adaptor and calculate the tidal and minute flows from these values;

e—detect the start of inhalation from either the temperature and humidity profiles of prior inhaled and exhaled gas samples, or from the differential pressure values generated by the membrane in the optional auxiliary adaptor, and operate the suction system of the monitoring unit for short durations during this period in order to determine the inhaled gas relative humidity and temperature without being affected by the humidity sensor's time constant;

f—analyze the degree of optimization between lung perfusion and lung ventilation based on the observed heat exchange rates and dynamic temperature profiles of exhaled gases for a given combination of variables in the inhaled gases. This may be done with the patient under ongoing ventilation conditions, or subjected to an abrupt change in the temperature and/or humidity of the inhaled gas and/or of the minute volume;

g—access and display previously recorded data and trends therein to permit comparison to most recently collected data and/or to typical Qi values of comparable individuals;

h—regulate the heating resistors and/or the LED within the measuring chamber in order to remove condensation from the measuring chamber before a reading is taken (to minimize evaporation-induced measurement errors) or to "condition" the relative humidity sensors when required prior to data acquisition. Humidity sensor conditioning entails the heating thereof during the inhalation phase between data sampling sessions in order to restore optimal sensor response characteristics; and i—regulate the heating resistors and/or an LED within the measuring chamber to remove condensation from the tubing linking the measuring chamber to the monitoring unit to prevent a build-up of moisture in the tubing, which may interfere with suction pump operation.

In preferred embodiments, a self-diagnostic application is additionally embedded in the processing and control circuitry to warn users when device operating parameters are outside of specified limits. Standard health care protocol may also be provided to facilitate the transmission of acquired patient data to a central monitoring and data storage system within medical facilities such as hospitals, clinics, etc.

All of the methods and tasks described herein, excluding those identified as performed by a human, may be performed and fully automated by a computer system, and may be embodied in software code modules executed by one or more general purpose computers. The code modules may be stored in any type of computer-readable medium or other computer storage device. Some or all of the methods may alternatively be embodied in specialized computer hardware. The computer system may, in some cases, include multiple distinct computers or computing devices (e.g., mobile devices, physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium. Where the system includes multiple computing devices, these devices may, but need not, be co-located. The results of the disclosed methods and tasks may be persistently stored by transforming physical storage devices, such as solid state memory chips and/or magnetic disks, into a different state.

BRIEF DESCRIPTION OF THE DRAWINGS

For a fuller understanding of the nature and advantages of the disclosed subject matter, as well as the preferred mode of use thereof, reference should be made to the following detailed description, read in conjunction with the accompanying drawings. In the following drawings, like reference numerals designate like or similar parts or steps.

DETAILED DESCRIPTION

Figure 1:
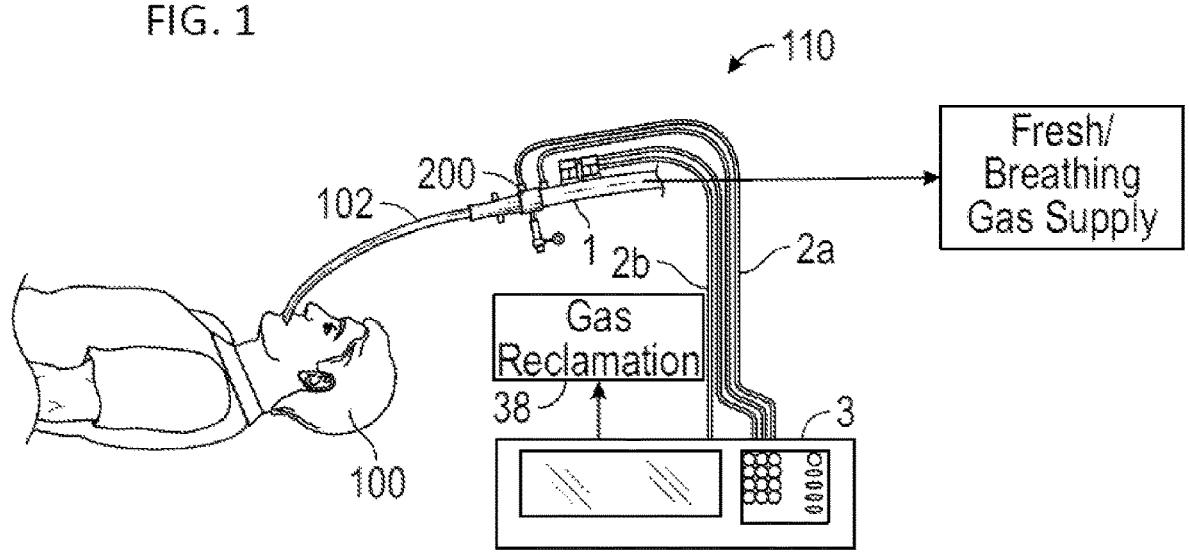
FIG. 1 is a schematic functional diagram of an apparatus in accordance with an embodiment of the disclosed subject matter, showing the main components thereof in relation to a patient.
Figure 2:
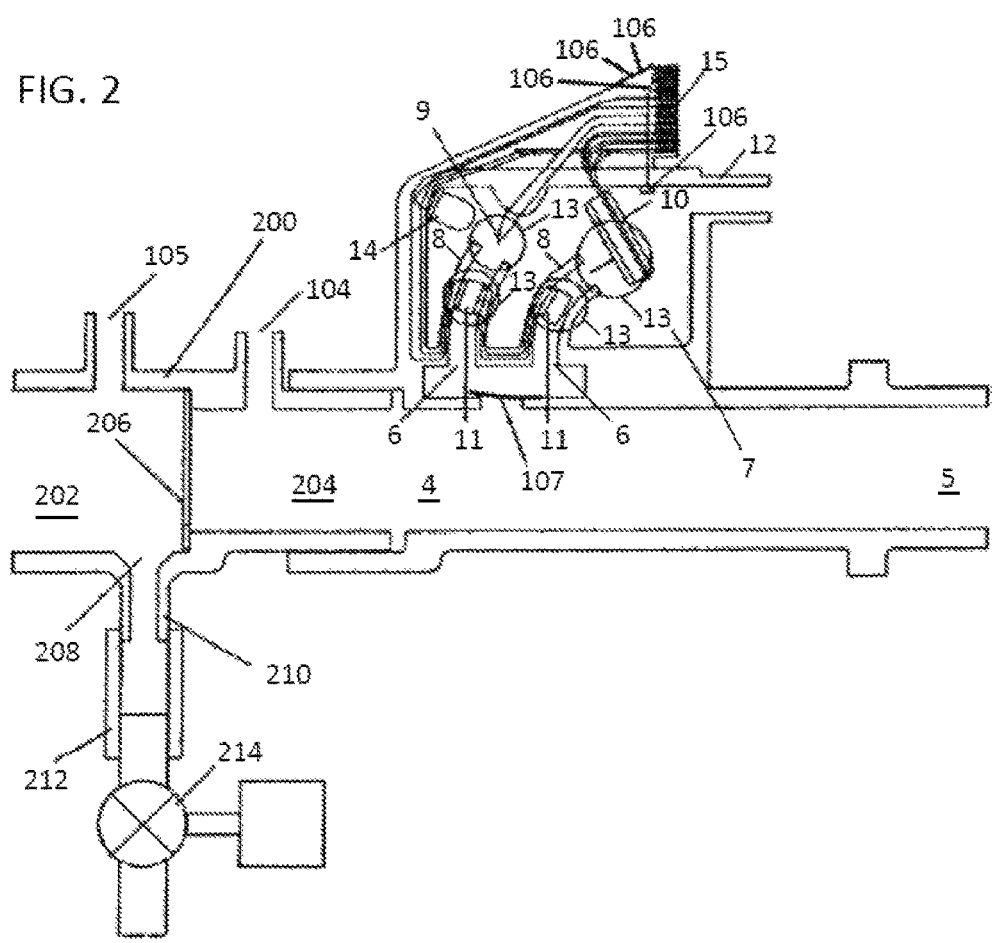
FIG. 2 is an enlarged cross-sectional side elevation of the adaptor/measuring chamber element of the apparatus of FIG. 1.

Referring to FIG. 1, a system and apparatus for assessing the coupling between lung perfusion and ventilation in a patient 100 who is mechanically ventilated or who is breathing spontaneously through a conventional artificial airway 102 is provided and generally designated with reference numeral 110. The apparatus generally comprises an adaptor/measuring chamber 1 configured for connection to artificial airway 102, either directly or, as illustrated, via auxiliary adaptor 200, and to a remote monitoring unit 3 via conventional plastic tubing 2a and electrical wiring 2b. In typical embodiments, the plastic tubing 2a is of conventional 2- or 3-lumen configuration and has an internal diameter of 2.4 mm or less, and the electrical wiring comprises 7 to 12 discrete wires, all of which are fitted with conventional mechanical and electrical connectors at each end.

The illustrated embodiment of adaptor/measuring chamber 1 is shown as being formed from a single molded piece, but the adaptor and measuring chamber portions thereof may alternatively be formed from separate moldings or castings. Inlet 4 and outlet 5 of adaptor/measuring chamber 1 are shaped and configured to connect, respectively, to conventional artificial airway 102 (or to auxiliary adaptor 200) and to a conventional mechanical ventilator, and define a main airflow path 4-5 therebetween through the adaptor portion of adaptor/measuring chamber 1.

Sampling port or ports 6 permit gases to be drawn from the main airflow path 4-5 into the measuring chamber portion 7 of adaptor/measuring chamber 1 via one or more ducts 8 integrated into the molding and sized to maintain the same gas/air flow speed as in the artificial airway 102, or a selected ratio thereof. A thin-wire fast response (typically 2 mS) temperature sensor or thermocouple 9 and a fast response (typically 3 sec) relative humidity ("RH") sensor 10 are positioned adjacent the outlet of the ducts 8 to optimize response time. Surface mounted and mechanically secured heating resistors 11 may be located in the ducts 8, and when present may be used to compensate for heat losses incurred during the transfer of gases into the measuring chamber 7, and to displace (i.e. lower) the relative humidity levels of the gases by a selected specific amount to improve the performance of the RH sensor. Heating resistors 11 may also act as mucous interceptors, evaporators or measuring chamber 7 driers, and may also be used to verify the gas flow rate passing through the measuring chamber 7 by comparing the time that it takes the thermocouple 9 to detect a given temperature rise vis-a-vis the time taken for a corresponding temperature rise to occur during calibration with a known gas flow rate.

Gases drawn through the measuring chamber 7 exit to tubing 2a and thence on to monitoring unit 3 through a chamber outlet 12 that is preferably located in a position remote from the sampling port(s) 6, and that may comprise a Luer-Lok™ male connector. In embodiments where an optional auxiliary adaptor 200 is used, outlets 104 and 105, also comprising male connectors and located remote from the sampling port(s) 6, are also be provided for transmitting pressure signals via tubing 2a to a spirometry module 32 in the monitoring unit 3.

The adaptor/measuring chamber 1 is preferably constructed of clear rigid plastic material, and may additionally comprise up to three photo sensors 106 orthogonally aligned in three dimensions and associated circuitry to enable the automatic detection of inclination of the adaptor/measuring chamber 1 by comparing the difference in the ambient light reaching each of the photo sensors 106. In alternative embodiments, photo sensors 106 may be replaced with a 3-axis accelerometer to achieve the same purpose. Optional one-way flap 107 may also be provided between the main airflow path 4-5 and measuring chamber portion 7 of the adaptor/measuring chamber 1 to minimize humidity migration into measuring chamber 7 during the exhalation phase.

The measuring chamber 7 may also include one or more molded-in plano-convex or double-convex lenses 13 suitably positioned to provide an enlarged view of the temperature sensor (i.e. thermocouple) 9, the measuring surface of the relative humidity sensor 10, and the heating resistors 11. An LED 14 may also be mounted within measuring chamber 7 to illuminate the thermocouple 9, the relative humidity sensor 10 and the heating resistors 11. Lenses 13 and LED 14 thereby permit, where present, an operator to readily check for the presence of mucous or other undesirable matter on the sensors 9, 10 and/or resistors 11. The intensity of LED 14 may be also modulated to provide heating to compensate for heat losses across the walls of measuring chamber 7. All chamber component wiring terminates at an electrical connector 15 for connection to monitoring 3 via wiring 2b.

Auxiliary adaptor 200 comprises a length of molded clear rigid plastic tubing with an inlet 202 and an outlet 204 shaped and configured to connect, respectively, to artificial airway 102 and to inlet 4 of adaptor/measuring chamber 1, and define a main airflow path 202-204 therebetween through auxiliary adaptor 200. A membrane 206 comprising a flexible flap provides resistance to the airflow through auxiliary adaptor 200, and the relative pressures generated by this resistance are transmitted via outlets 104 and 105 and flexible tubing 2a to spirometry module 32 in the monitoring unit 3. A drain 208 molded in the auxiliary adaptor intercepts mucous and fluids, and allows them to be readily removed via drain outlet 210. Outlet 204 of auxiliary adaptor 200 is preferably keyed to fit the adaptor/measuring chamber 1 with drain 208 positioned at 180 degrees relative to the vertical orientation of the measuring chamber 7 to further facilitate proper drainage of mucous and fluids. Drain outlet 210 is connected to tubing 212 and a manually or automatically operated drain valve 214. In preferred embodiments, the automatic drain valve 214 is actuated during an exhalation cycle and when the system is not sampling data.

Figure 3:
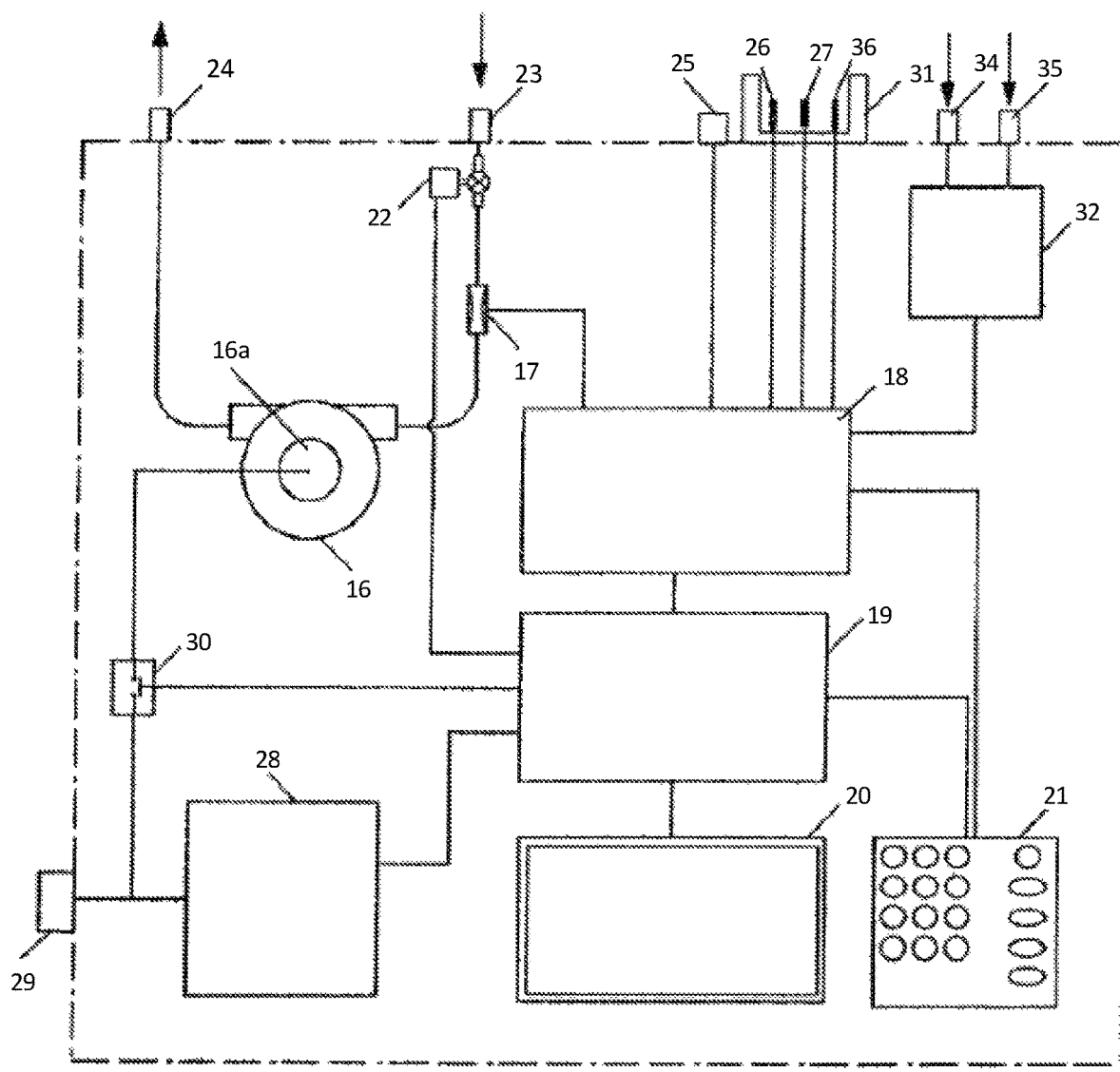
FIG. 3 is a schematic diagram of the monitoring unit element of the apparatus of FIG. 1.

Schematically illustrated in FIG. 3, monitoring unit 3 comprises a small capacity diaphragm suction pump 16 with an optional heated head 16a, flow meter or thermocouple 17, data acquisition, conversion, storage and display module 18, control module 19, LCD touch screen display and driver 20, keypad 21, solenoid shut off valve 22, air inlet connection 23 for receiving gases drawn through tubing 2 from measuring chamber outlet 12, air outlet connection 24, wire connector 25 for communication via wires 2b with electrical connector 15 of measuring chamber 3, reference thermistors 26 and 36, reference relative humidity sensor 27, and conventional power supply module 28 to provide DC power thereto. AC power is provided to the power supply module 28 via receptacle 29, and to the pump 16 via relay 30. For calibration at start-up, a bracket 31 is provided on monitoring unit 3 to hold the adaptor/measuring chamber 1 in a suitable position for directing airflow over the reference thermistors 26 and 36 and relative humidity sensor 27. In some embodiments, a spirometry module 32 is also included and is connected to pressure ports 34 and 35.

If present, the heated head 16a of pump 16 reduces the mechanical deterioration of pump 16 components due to high humidity and condensation. Air outlet 24 is preferably connected to a conventional gas reclamation or scavenging system 38.

The monitoring unit 3 is typically located at the site of patient care and is connected to the electrical mains via receptacle 29. The display and operator input portions 20, 21 of the monitoring unit 3 can be duplicated or physically separated from the remaining components of monitoring unit 3, and may, for example, be mounted at a clinical work station, which may be located remote from the site of patient care.

The data acquisition, conversion, storage and display module 18 of monitoring unit 3 preferably comprises an electronic circuit board (referred to herein as the "Data Acquisition Conversion Storage and Display" or "DACSD" board) configured to receive signals from the thermocouple 9 and relative humidity sensor 10 of measuring chamber 7, as well as from reference thermistors 26 and 36, reference relative humidity sensor 27, flow meter or thermocouple 17, spirometry module 32, touch-screen display 20 and keypad 21, and to automatically calculate Qi under control of software instructions as a weighted function of heat gain in one or more breathing cycles, the tidal or minute volume entered by the operator or determined by other means (such as by use of a spirometry module as herein described), the type of ventilation change introduced (or not) by the operator, anthropometric patient data entered manually by the operator, and the parameters of the exhaled air temperature profile.

In general form, $Qi=k_1 \Delta H \times k_{nb} \times k_v \times k_{pr} \times k_{pa}$, where H is air flow enthalpy, and $k_1$, $k_{nb}$, $k_v$, $k_{pr}$, and $k_{pa}$ are weighing factors stored in system memory or calculated from manually entered or sensor acquired data. Any change in any of the weighing factors will accordingly have a direct impact on the Qi. $k_1$ is calculated as a function of tidal volume; $k_{nb}$ as a function of breathing rate; $k_v$ as a function of the ventilation change, if any, introduced by the operator of a mechanical ventilator; $k_{pr}$ as a function of anthropometric patient data entered by the operator; and $k_{pa}$ as a function of exhaled air temperature profile.

Since the Qi index is expressed in non-dimensional units and is displayed relative to a range of "normal" values (defined with reference to values that are commonly observed at rest in persons in good general health and who generally match a given patient in gender, age and body size, and/or as a specific patient's baseline values at rest or under stress at the outset of a monitoring interval), and since ongoing diagnostic cardio-pulmonary monitoring of a patient is carried out by comparing changes in the patient's Qi index during a monitoring interval, the specific methodology utilized in the derivation of numeric values for each of the weighing factors $k_1$, $k_{nb}$, $k_v$, $k_{pr}$, and $k_{pa}$ is not critical, so long as whatever methodology is chosen is consistently applied as between the derivation of the patient's values and the reference values against which the patient's Qi index is evaluated.

For artificially ventilated patients, ventilation may typically include one or more of: (a) switching from heated and humidified gas to gas of a different composition, (b) changing the tidal volume, and (c) changing the ventilation rate. The tidal volume $k_1$ in this implementation may be entered by the operator or determined by other means as previously described.

Additional functions of the DACSD module 18 may include:

a—the conversion of the sampling data generated by the relative humidity sensors 10, 27; thermocouples 9, 17; and thermistors 26, 36 into temperature and humidity readings;

b—the calculation and application of correction values for the readings of the measuring chamber relative humidity sensor 10 by comparison with the readings of the reference relative humidity sensor 27 and the heating resistors' 11 operation;

c—the conversion of data from the spirometry module 32 into tidal and minute volume values;

d—monitoring of the inclination of the measuring chamber 7 relative to its preferred position along a vertical axis atop the adaptor portion of adaptor/measuring chamber 1 by comparison of readings from each of the photo sensors (or accelerometer) 106, and preferably including the triggering of an alarm if the inclination exceeds a predetermined maximal value;

e—checking for the sampling gas flow value at start-up and periodically thereafter via the direct flowmeter 17, or by measuring the temperature rise when the heating resistors 11 are activated and comparing it to the expected temperature rise for a given suction pump 16 airflow level;

f—determining the sequence of operation of the suction pump 16, the solenoid valve 22 and the heating resistors 11 using data received from the sensors of the measuring chamber 7 and of the monitoring unit 3, the keypad 21 the touch screen 20 and an internal timer;

g—transmission of converted data to the display driver 20;

h—retrieving and displaying previously calculated Qi's, Qi trends, and other derived value profiles for the patient undergoing testing, or for typical cases stored in memory;

i—detecting and initiating recovery measures when an abnormal condition involving condensation or mucosal secretions occurs, and shutting down the system if the recovery attempt fails;

j—determining the additional heating required to compensate for heat loss of the gas in transit from the airway to chamber 7 with respect to ambient temperature, and transmitting this data to the control board 19;

k—determining the RH displacement when the heating resistors 11 are in operation;

l—determining the level and duration of the condensation clearing cycle prior to logging of the sampled gas flow data, and transmitting this the data to the control board 19;

m—determining the timing of the fluid clearing routine from the auxiliary adaptor 200 with respect to sampling cycles and preset or automatically determined time intervals;

n—monitoring the moisture content in suction pump 16 during shut down of the monitoring unit 3 to ensure the pump 16, solenoid 22 and flow meter or thermocouple 17 are clear of moisture before power is turned off;

o—issuing warning messages when unusual data (such as, for example, a humidity drop to 0%, or a temperature reading below ambient) indicates a fault in the equipment or its performance;

p—issuing a visual and audio warning message if a trend consistent with a deterioration of a patient's condition (signaled by a decreasing Qi index number) is detected; and, q—optionally transmitting display data and alert messages to a remote/central monitoring station.

The control board 19 receives data from the DACSD 18, the keypad 21 and the touch-screen display 20. The functions of the control board 19 include:

a—conditioning and providing the required DC power to the DACSD 18, the display 20, the keypad 21, the solenoid valve 22, the RH sensors 10, 26, 36, the heating resistors 11, the LED 14 and the pump-head heater 16a;

b—controlling and monitoring the AC or DC power going to the pump 16, and signal a warning if a set current threshold is crossed or if a suspicious trend (such as an unexpected incremental decrease of power consumption, likely indicating pump diaphragm failure, or an unexpected incremental increase in power consumption, likely indicating blockage of tubing 2a or a failing pump motor) develops;

c—pulsing the power supply to the pump 16 in synchronicity with inhalation periods in order to operate pump 16 for typically 1.0 seconds after a short initial delay of typically 0.2 seconds following the start of inhalation, thereby to synchronize the apparatus for sampling of only inhaled air conditions (as required where inhaled air parameters are not keyed in manually);

d—monitoring the wiring 2b between the measuring chamber 7 and monitoring unit 3, and shut down all power if a ground fault is detected;

e—providing routine electrical safety monitoring and response; and, f—opening and closing the fluid removal solenoid valve at the auxiliary adaptor outlet.

In use of the subject system and apparatus 110, the power is turned on and a fully connected adaptor/measuring chamber 1 is first fitted over bracket 31 of monitoring unit 3 (prior to the connection of the adaptor/measuring chamber 1 to the artificial airway 102) for initial calibration of measuring chamber temperature sensor 9 and relative humidity sensor 10 as against reference thermistor 26 and reference relative humidity sensor 27 of monitoring unit 3. Reference relative humidity sensor 27 may itself be calibrated periodically by running the standard calibration procedure and using one of the reference thermistors 26, 36 for wet bulb readings (by using a wet sleeve fitted to it) against a dry bulb reading provided by the other reference thermistor 26, 36. Bracket 31 additionally holds the adaptor/measuring chamber 1 in a suitable position to permit the operator to check for defects and for correct gas flow through adaptor/measuring chamber 1.

Once initial calibration is complete, the adaptor/measuring chamber 1 is removed from bracket 31, and in embodiments that include an auxiliary adaptor 200, the adaptor/measuring chamber 1 is then connected to the auxiliary adaptor 200 before the auxiliary adaptor 200 is connected to the artificial airway 102. In embodiments where no auxiliary adaptor 200 is used, the adaptor/measuring chamber 1 is connected directly to the artificial airway 102.

The operator then initiates the sampling sequence manually or automatically via a timer set from the keypad 21 or from the display touch-screen 20. The sampling sequence starts the suction pump 16 and the flow of gases through the measuring chamber 7. By timing the interval between the low and/or high temperature and/or humidity plateaus between inhalations and/or exhalations (or the pressure reversal points in embodiments that employ auxiliary adaptor 200), the apparatus detects the breathing phases (i.e. the duration of inhalation and exhalation), initiates the inhaled gas measurement cycle followed by the full measurement cycle and logs the contemporaneous sensor readings.

A typical sequence of events experienced by a patient during a testing session using the subject system and apparatus 110 may comprise:

a—An initial keying-in via keypad 21 and/or touch-screen display 20 of patient data including, among other potential characteristics, the weight, height, gender, and age of the patient, and in some preferred embodiments where the apparatus is set up to send data to a patient data storage location (e.g. to a hospital information system), a unique patient identifier;

b—If clinical circumstances permit, obtaining "baseline" samples of the patient's Qi and storing these in DACSD module 18;

c—Next, sampling at pre-determined intervals and/or at the prompt of the operator with or without a concurrent transient change in the hydrothermal profile of the inhaled gases is carried out. The apparatus 110 tracks the type of changes, if any, induced in the inhaled gases, and the type of ventilation change that is induced is keyed in or left to the system to track;

d—The sampling sequence typically starts with determining the inhaled gas temperature and humidity by running the suction pump 16 for typically one or two seconds within several inhalation periods. A full sampling then follows (typically for roughly 30 seconds), and the acquired temperature and humidity data is continuously logged and used for the generation of graphical displays and for calculating the heat exchange values in the patient's lungs with respect to the inhalation parameters;

e—The inhaled gas sampling procedure outlined in step (d) above may also be used to determine the exhaled gas temperature and humidity, and this data may alternately be used to calculate the heat exchange values, or as a cross-check for the heat exchange values calculated in accordance with step (d);

f—The values of the Qi over the course of the patient observation period are calculated, monitored and analyzed by the system and presented visually to the operator. The apparatus will provide an alarm signal if a trend in the Qi or in the temperature or humidity profiles shows a deterioration in the patient's clinical status.

g—The apparatus also calculates and measures trends (salutary or otherwise) and displays these in a color coded manner. Improvement or deterioration coding will be relative to previous readings for the same patient, or relative to "in good health" values for persons of similar stature, gender and age The present description includes the best presently contemplated mode of carrying out the subject matter disclosed and claimed herein, and is made for the purpose of illustrating the general principles of the subject matter and not be taken in a limiting sense; the subject matter can find utility in a variety of implementations without departing from the scope of the disclosure made, as will be apparent to those of skill in the art from an understanding of the principles that underlie the subject matter.

We claim:

1. An apparatus for assessing and monitoring ventilation-perfusion coupling in a patient who is mechanically ventilated through an artificial airway or breathing spontaneously through the artificial airway, the apparatus comprising:
    an adaptor providing a main path for gases inhaled and/or exhaled by the patient;
    a measuring chamber in fluid communication with the adaptor and partitioned from the main path of the gases inhaled and/or exhaled by the patient through the adaptor, the measuring chamber comprising temperature and relative humidity sensors for measuring the temperature and humidity of the gases inhaled and/or exhaled by the patient; and
    a monitoring unit in fluid and electrical communication with the measuring chamber, the monitoring unit comprising:
        a thermocouple or a flow meter;
        a suction pump for drawing the inhaled and/or exhaled gases from the adaptor and through the measuring chamber and the thermocouple or the flow meter;
        a display and a data entry means; and
        a monitoring unit control system to receive a signal from the temperature and relative humidity sensors, from the thermocouple or the flow meter, and from an operator of the system, wherein the monitoring unit is configured to:
    a) store patient data values entered by the operator via the data entry means;
    b) detect a plurality of breathing phases of the patient by determining an interval between a low and/or high temperature and/or humidity plateaus between individual inhalations and/or exhalations as measured by the temperature and/or relative humidity sensors;
    c) obtain and store base heat exchange values from the measured temperature and relative humidity of the inhaled and/or exhaled gases by activating the suction pump at a prompt of the operator or according to a pre-determined interval to draw air past the temperature and humidity sensors in the measuring chamber, and then repeatedly sample the temperature and relative humidity of the inhaled and/or exhaled gases to obtain and store a plurality of sampled heat exchange values during a monitoring interval;
    d) compare a first one of the plurality of sampled heat exchange values against the base heat exchange values, and compare each successive one of the plurality of sampled heat exchange values against a preceding one of the sampled heat exchange value to calculate and store a heat gain value corresponding to each of the plurality of sampled heat exchange values;
    e) multiply the stored patient data values and a difference between two or more of the stored heat gain values to derive a non-dimensional coupling index; and
    f) display the calculated coupling index to the operator via the display means during the monitoring interval relative to pre-defined normal values.

2. The apparatus of claim 1, wherein the stored patient data values can include a tidal volume of the patient, a minute volume of the patient, a breathing rate of the patient, a ventilation change of the patient, an exhaled air temperature profile of the patient, one or more patient anthropometric inputs and/or any combination thereof.

3. The apparatus of claim 2, further comprising an auxiliary adaptor configured to fit between the artificial airway and the adaptor, wherein the auxiliary adaptor includes a flexible membrane to create pressure differentials by resisting airflow therethrough, and a spirometer in fluid communication therewith to measure tidal or minute volume for entry into the stored patient data.

4. The apparatus of claim 1, wherein the monitoring unit further comprises reference temperature and relative humidity sensors, and wherein the monitoring unit is configured, prior to step (a), to initially calibrate the measuring chamber temperature and relative humidity sensors readings relative to the reference temperature and relative humidity sensor readings.

5. The apparatus of claim 1, wherein the measuring chamber further comprises one or more heating resistors to compensate for heat losses incurred during the transfer of the inhaled and/or exhaled gases into the measuring chamber, and wherein the monitoring unit is configured to calculate and apply suitable compensatory factors by activation of the heating resistors.

6. The apparatus of claim 1, wherein the calculated coupling index is displayed relative to pre-defined normal values, wherein the pre-defined normal values are defined by one or more baseline values based on personal characteristics of the patient at rest and/or under stress, and/or one or more reference values based on characteristics of a population predetermined to indicate desired health.

7. An automated diagnostic method for assessing and monitoring ventilation-perfusion coupling in a patient who is mechanically ventilated or breathing spontaneously through a conventional artificial airway by use of an apparatus comprising:
    an adaptor providing a main path for gases inhaled and/or exhaled by the patient;
    a measuring chamber in fluid communication with the adaptor and partitioned from the main path of the gases inhaled and/or exhaled by the patient through the adaptor, the measuring chamber comprising temperature and relative humidity sensors for measuring the temperature and humidity of the gases inhaled and/or exhaled by the patient; and
    a monitoring unit in fluid and electrical communication with the measuring chamber, the monitoring unit comprising:
        a thermocouple or a flow meter;
        a suction pump for drawing the inhaled and/or exhaled gases from the adaptor and through the measuring chamber and the thermocouple or the flow meter;
        a display and a data entry means; and
    a monitoring unit control system to receive data acquired from the temperature and relative humidity sensors, from the thermocouple or the flow meter, and from an operator of the system,
    the method comprising:
        storing patient data values entered by the operator via the data entry means;
        detecting a plurality of breathing phases of the patient by determining an interval between a low and/or high temperature and/or humidity plateaus between individual inhalations and/or exhalations as measured by the temperature and/or relative humidity sensors;

obtaining and storing base heat exchange values from the measured temperature and relative humidity of the inhaled and/or exhaled gases by activating the suction pump at a prompt of the operator or according to a pre-determined interval to draw air past the temperature and humidity sensors in the measuring chamber, and then repeatedly sampling the temperature and relative humidity of the inhaled and/or exhaled gases to obtain and store a plurality of sampled heat exchange values during a monitoring interval;

comparing a first one of the plurality of sampled heat exchange values against the base heat exchange values, and compare each successive one of the plurality of sampled heat exchange values against a preceding one of the sampled heat exchange value to calculate and store a heat gain value corresponding to each of the plurality of sampled heat exchange values;

multiplying the stored patient data values and a difference between two or more of the stored heat gain values to derive a non-dimensional coupling index; and displaying the calculated coupling index to the operator via the display means during the monitoring interval.

* * * * *